United States Patent
Gerber et al.

Patent Number: 5,741,335
Date of Patent: Apr. 21, 1998

[54] TOTAL SHOULDER PROSTHESIS

[75] Inventors: Christian Gerber, Zumikon, Switzerland; Yves Pequignet, Chalonvillars, France

[73] Assignee: Cedior, Etupes Cedex, France; a part interest

[21] Appl. No.: 665,017

[22] Filed: Jun. 11, 1996

[51] Int. Cl.⁶ .................................. A61F 2/40; A61F 2/32
[52] U.S. Cl. ...................................... 623/19; 623/22
[58] Field of Search ........................ 623/18, 19, 22, 623/23, 48; 403/128–131, 72, 74

[56] References Cited

U.S. PATENT DOCUMENTS

| | | | |
|---|---|---|---|
| 3,429,598 | 2/1969 | Scheublein, Jr. et al. | 403/128 |
| 3,916,451 | 11/1975 | Buechel et al. | 623/19 |
| 4,030,143 | 6/1977 | Elloy et al. | 623/19 |
| 4,279,041 | 7/1981 | Buchholz | 623/19 |
| 4,504,165 | 3/1985 | Moeremans | 403/129 |
| 4,838,795 | 6/1989 | Draenert | 623/23 |

FOREIGN PATENT DOCUMENTS

| | | |
|---|---|---|
| A-2689756 | 10/1993 | France . |
| A-2701206 | 8/1994 | France . |
| WO 93/09733 | 5/1993 | WIPO . |

*Primary Examiner*—Michael J. Milano
*Assistant Examiner*—Tram Anh T. Nguyen
*Attorney, Agent, or Firm*—Nilles & Nilles SC

[57] ABSTRACT

A shoulder prosthesis includes a humeral stem designed to be implanted within the patient's humeral canal and a head portion designed to cooperate with the glenoid cavity of a shoulder. The head portion, which has a spherical shape generated by revolution about an axis, is connected to the humeral stem by a link that includes 1) a ball fixed to a proximal end of the stem and 2) a spherical socket made in the head portion and forming a housing for the ball. The axis of revolution of the head portion is off-set with respect to the center of the ball. The assembly formed by the socket and the ball constitutes a joint capable of making the orientation of the head portion vary in relation to the stem by rotation about the center of the ball. The head portion is lockable to the stem, preferably by a conical push rod which moves into an axial conical bore under the action of a tightening screw, to cause compression of the ball against the spherical cavity by blocked lateral expansion of the ball.

8 Claims, 2 Drawing Sheets

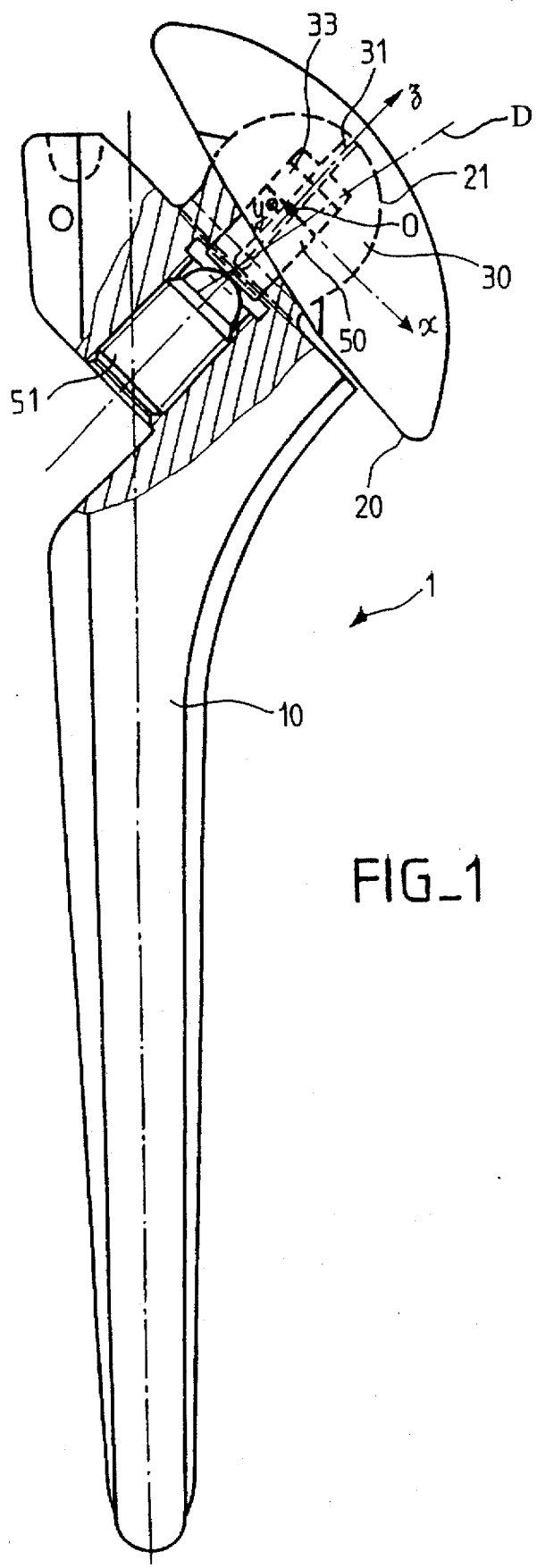
FIG_1

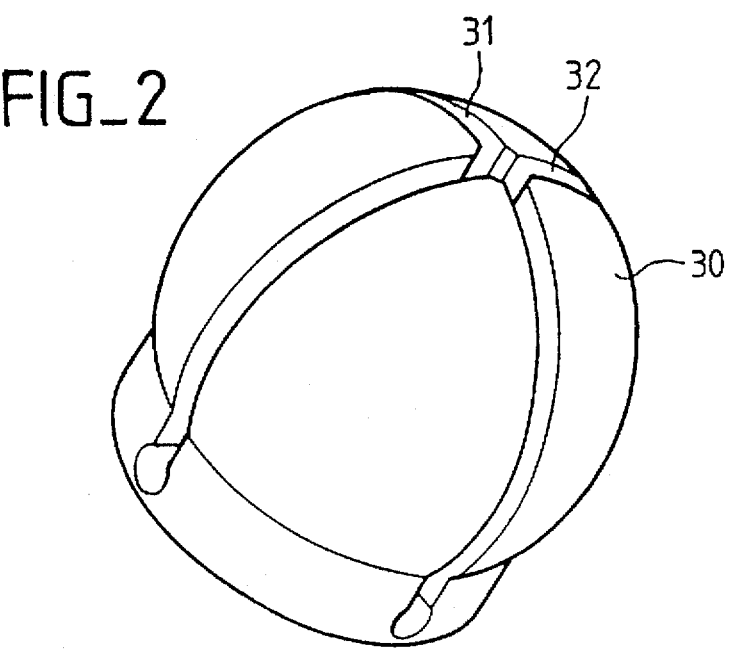
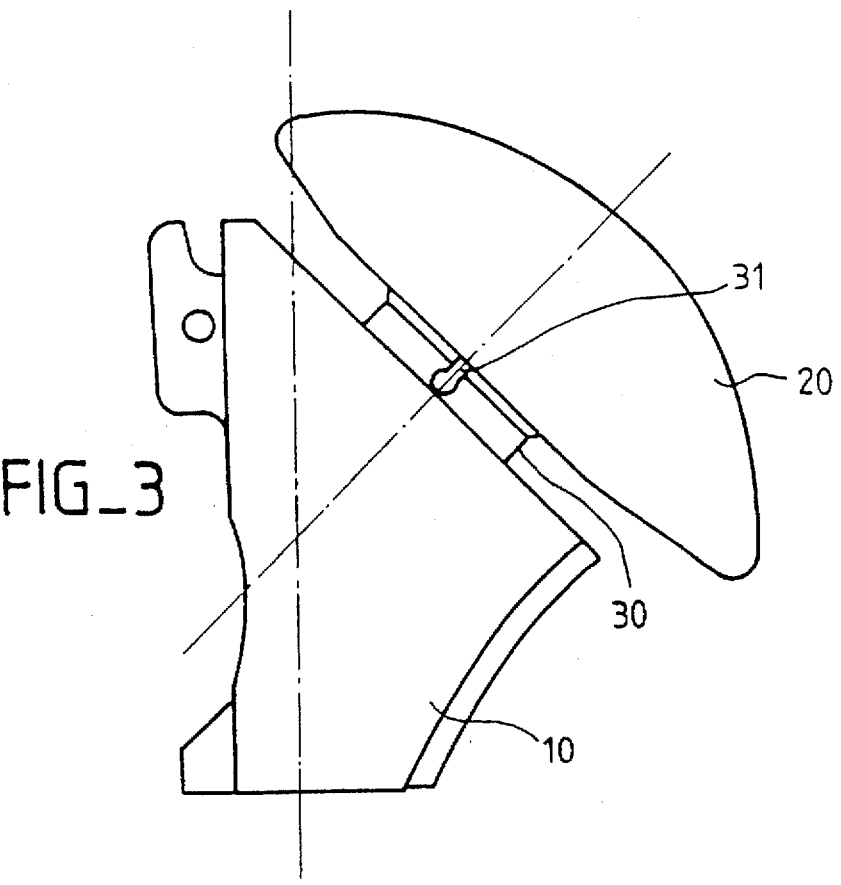

TOTAL SHOULDER PROSTHESIS

BACKGROUND OF THE INVENTION

1. Field of the Invention

The invention relates to a total shoulder prosthesis.

The invention can be applied with particular advantage to the treatment of degenerative diseases such as glenohumeral arthrosis and those related to the traumatology of the shoulder joint.

2. Description of the Prior Art

In general, there are prior art total shoulder prostheses comprising a humeral stem designed to be implanted within a patient's humeral canal, this stem having a head portion with a spherical shape generated by revolution, designed to cooperate with the glenoid cavity of the shoulder, whether prosthetic or not.

In particular, there are prostheses of this type where the stem is called a single-piece or unitary stem inasmuch as the spherical head portion of the humerus is part of the stem itself. The NEER model is the best example of this kind of prosthesis.

However, apart from the fact that such devices require the setting up of large inventories, these prior art prostheses have the drawback of not enabling any medial offset, or eccentric positioning, characterized by the intersection of the proximal metaphysis axis with the periphery of the joint-forming head portion. Furthermore, since their tilt is fixed, they do not satisfactorily overlap the sectional plane of the end of the humerus. Finally, there is no possibility of envisaging an adjustment in retroversion with these unitary prostheses.

Again, other models of humeral stems use wedge-shaped shims placed between the stem and the head portion to obtain tilts of this spherical head portion that vary sequentially by steps. These same stems also permit a certain adjustment of the medial offset by rotation of the spherical head portion about an axis that is eccentric with respect to its geometrical axis. However, here again, the possibilities of adjustment are limited because this adjustment can be done only on a finite number of discontinuous positions. It will furthermore be noted that even if they are an improvement on unitary prostheses, these prior art humeral stems provide no answer to the question of adjustment in retroversion.

SUMMARY OF THE INVENTION

Thus, the technical problem to be resolved by the object of the present invention is that of proposing a total shoulder prosthesis comprising:

- a humeral stem designed to be implanted within the patient's humeral canal,
- a head portion with a spherical shape generated by revolution about an axis designed to cooperate with the glenoid cavity of the shoulder,
- this prosthesis being provided with means for the continuous adjustment and not solely the discrete adjustment, of the spherical head portion in all possible orientations, including retroversion, with respect to the humeral stem, thus enabling the reproduction of the exact anatomy of the shoulder.

According to the solution provided by the present invention to the technical problem posed, this prosthesis comprises:

means to link this head portion to the humeral stem, comprising a ball fixed to a proximal end of the stem, and a spherical socket made in this head portion and forming a housing for this ball, the axis of revolution of the spherical head portion being offset with respect to the center of this ball, the assembly formed by the socket and the ball constituting a joint capable of making the orientation of the spherical head portion vary in relation to the stem by rotation about the center of the ball, means for the locking of the head portion in position on the ball.

Thus, these linking means enable the obtaining of all three motions required for the spherical head portion, namely the movements of tilting, medial offset owing to the offset of the axis of revolution of the head portion with respect to the center of the ball and lateral retroversion. Naturally, these motions are achieved in a perfectly continuous way and in all their possible combinations. This ensures a very precise reconstitution of the anatomy of the shoulder.

According to a particular embodiment of the invention, the locking means comprise, firstly, at least one median slot and one axial conical bore leading into this median slot, this slot and this bore being made in the ball and, secondly, a conical push-rod positioned in the stem and activated by a tightening screw in such a way as to exert a force of pressure on the conical bore prompting compression against the spherical cavity through blocked lateral expansion of the ball.

BRIEF DESCRIPTION OF THE DRAWINGS

The following description made with reference to the appended drawings, given by way of non-restrictive examples, shall provide a clear understanding of the content of the invention and the way in which it can be achieved.

FIG. 1 is a partial sectional view of a total shoulder prosthesis according to the invention.

FIG. 2 is a view in perspective of a particular embodiment of a ball enabling the locking of the head portion of FIG. 1.

FIG. 3 is a side view showing the head portion of FIG. 1 in position on the ball of FIG. 2.

MORE DETAILED DESCRIPTION

FIG. 1 shows a partial sectional view of a total shoulder prosthesis 1 comprising a humeral stem 10 designed to be implanted inside the patient's humeral canal. Furthermore, a spherical head portion 20 with an axis of revolution D is designed to cooperate with the glenoid cavity of the shoulder of the patient.

As can be seen in FIG. 1, this shoulder prosthesis 1 has means to link the head portion 20 with the humeral stem 10 comprising a ball 30 with a center 0 fixed to a proximal end of the stem 10 while a spherical cavity 21 made in the head portion 20 forms a housing for the stem 30. It can be seen in FIG. 1 that the axis of revolution D of the spherical head portion 20 is offset from the center 0 of the ball 20.

The rotational motions of the head portion 20 may be subdivided into three elementary rotations: one rotation about an axis Oy transversal to the stem 10 and perpendicular to the axis Oz of the ball 30 that enables the tilting of the head portion 20, another rotation about the axis Oz corresponding to the eccentricity or medial offset of the spherical head portion 20 resulting from the offset of the axis of revolution D of the head portion with respect to the center 0 of the ball 30 and, finally, the rotation about the axis Ox that achieves the lateral retroversion of the head portion, this additional degree of liberty being hitherto unknown in commonly used shoulder prostheses.

Another fact to be noted is the continuous character of these three rotational motions without any notion of adjustment by discrete steps as is the case in prior art prostheses. This advantage, associated with the one in which it is possible to have available all the degrees of liberty in rotation, enables a reproduction of the anatomy of the shoulder that is as exact as possible.

The spherical head portion 20 is then locked into position on the ball 30 through means comprising two orthogonal median slots 31, 32 made in the ball 30 to prevent any additional motion of the head portion with respect to the ball as can be seen in greater detail in the view in perspective shown in FIG. 2, the assembly formed by the head portion 20 and the ball 30 being shown in FIG. 3.

According to the embodiment shown in FIG. 1, an axial conical bore 33 leading into the median slots 31, 32 receives a conical push-rod 50. This conical push-rod 50 is controlled by a tightening screw 51 operated from outside the humeral stem 10 so as to exert a force of pressure on the conical bore 33 in order to cause compression against the spherical cavity 21 by the blocked lateral expansion of the ball 30.

What is claimed is:

1. A total shoulder prothesis comprising:

a humeral stem designed to be implanted within a patient's humeral canal, a head portion with a spherical shape generated by revolution about an axis designed to cooperate with the glenoid cavity of the shoulder, a link assembly connecting said head portion to the humeral stem, said link assembly comprising 1) a ball fixed to a proximal end of said stem and 2) a spherical socket located in said head portion and forming a housing for said ball, an axis of revolution of the head portion being offset with respect to the center of said ball, the socket and the ball constituting a joint capable of making the orientation of the head portion vary in relation to the stem by rotation about said center of the ball, and means for selectively locking the head portion in position on the ball so as to prevent any motion of the head portion with respect to the ball.

2. A prosthesis according to claim 1, wherein said means for selectively locking comprises means for expanding the ball into locking engagement with the spherical socket in the head portion.

3. A prosthesis according to claim 2, wherein the ball has a median slot and an axial conical bore formed therein to facilitate expansion thereof.

4. A total shoulder prosthesis comprising:

a humeral stem designed to be implanted within a patient's humeral canal, a head portion with a spherical shape generated by revolution about an axis designed to cooperate with the glenoid cavity of the shoulder, a link assembly connecting said head portion to the humeral stem, said link assembly comprising 1) a ball fixed to a proximal end of said stem and 2) a spherical socket located in said head portion and forming a housing for said ball, an axis of revolution of the head portion being offset with respect to the center of said ball, the socket and the ball constituting a joint capable of making the orientation of the head portion vary in relation to the stem by rotation about said center of the ball, and means for locking the head portion in position on the ball, wherein said means for locking comprise 1) at least one median slot and one axial conical bore leading into the median slot, the median slot and the axial conical bore being located in the ball, 2) a conical push-rod positioned in said stem, and 3) a screw which acts upon said conical push-rod in such a way that tightening the screw exerts a force of pressure on the axial conical bore of the ball that compresses the ball against the spherical socket in the head portion through blocked lateral expansion of the ball.

5. A method of positioning a total shoulder prosthesis comprising:

implanting a humeral stem within a patient's humeral canal;

providing a head portion with a spherical shape generated by revolution about an axis of revolution, the head portion being designed to cooperate with the glenoid cavity of the patient's shoulder, mounting a spherical socket of the head portion on a ball fixed to a proximal end of the stem, the spherical socket forming a housing for the ball, then varying the orientation of the head portion in relation to the stem by rotating the head portion about the center of the ball, said rotation occurring about an axis that is offset from the axis of revolution of the head portion, and then locking the head portion in position on the ball so as to prevent any motion of the head portion with respect to the ball.

6. A method according to claim 5, wherein the locking step comprises expanding the ball into locking engagement with the spherical socket in the head portion.

7. A method according to claim 6, wherein the ball has a median slot and an axial conical bore formed therein to facilitate expansion thereof during the expanding step.

8. A method according to claim 7, wherein the expanding step comprises tightening a screw to exert a force of pressure on the axial conical bore that compresses the ball against the spherical socket in the head portion through blocked lateral expansion of the ball.

* * * * *